US010806935B2

(12) United States Patent
Rao et al.

(10) Patent No.: US 10,806,935 B2
(45) Date of Patent: *Oct. 20, 2020

(54) NEUROSTIMULATION SYSTEM AND METHOD FOR CONSTRUCTING STIMULATION PROGRAMS

(71) Applicant: Boston Scientific Neuromodulation Corporation, Valencia, CA (US)

(72) Inventors: Prakash Rao, Philadelphia, PA (US); Sridhar Kothandaraman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 202 days.

This patent is subject to a terminal disclaimer.

(21) Appl. No.: 15/872,254

(22) Filed: Jan. 16, 2018

(65) Prior Publication Data

US 2018/0133492 A1 May 17, 2018

Related U.S. Application Data

(63) Continuation of application No. 13/856,230, filed on Apr. 3, 2013, now Pat. No. 9,895,545.

(Continued)

(51) Int. Cl.
*A61N 1/372* (2006.01)
*A61N 1/05* (2006.01)
*A61N 1/36* (2006.01)

(52) U.S. Cl.
CPC ........ *A61N 1/37247* (2013.01); *A61N 1/0551* (2013.01); *A61N 1/36071* (2013.01); *A61N 1/36128* (2013.01)

(58) Field of Classification Search
CPC .............. A61N 1/0551; A61N 1/36071; A61N 1/36128; A61N 1/37247
See application file for complete search history.

(56) References Cited

U.S. PATENT DOCUMENTS 6,516,227 B1 2/2003 Meadows et al.
6,895,280 B2 5/2005 Meadows et al.
(Continued)

FOREIGN PATENT DOCUMENTS

JP 2015512325 A 4/2015

OTHER PUBLICATIONS

"U.S. Appl. No. 13/856,230, Advisory Action dateded Jan. 25, 2016", 3 pgs.

(Continued)

*Primary Examiner* — Tan H Tran
(74) *Attorney, Agent, or Firm* — Schwegman Lundberg & Woessner, P.A.

(57) ABSTRACT

A device for use with a stimulation system comprises a user interface for receiving input from a user, displaying graphical parameter objects respectively corresponding to stimulation parameter sets, and displaying graphical program objects corresponding to stimulation programs. The device further comprises a controller/processor for selecting a graphical parameter object, dragging the graphical parameter object, dropping the graphical parameter object into a graphical program object, and storing the stimulation parameter set corresponding to the graphical parameter object in association with the stimulation program corresponding to the graphical program object. The user interface may further display graphical program objects corresponding to stimulation programs, and a graphical schedule object. The controller/processor may select a graphical program object, drag the graphical program object, drop the graphical program object into a time period of the graphical schedule object, and store the time period in association with the stimulation program corresponding to the graphical program object.

16 Claims, 12 Drawing Sheets

Related U.S. Application Data

(60) Provisional application No. 61/621,296, filed on Apr. 6, 2012.

(56) References Cited

U.S. PATENT DOCUMENTS

| | | | |
|---|---|---|---|
| 6,993,384 | B2 | 1/2006 | Bradley et al. |
| 7,519,431 | B2 | 4/2009 | Goetz et al. |
| 8,082,034 | B2 | 12/2011 | Keacher |
| 9,895,545 | B2 | 2/2018 | Rao et al. |
| 2004/0095390 | A1 | 5/2004 | Arning et al. |
| 2004/0199215 | A1 | 10/2004 | Lee et al. |
| 2007/0203544 | A1 | 8/2007 | Goetz et al. |
| 2007/0245300 | A1* | 10/2007 | Chan ............... G06Q 10/06 717/105 |
| 2008/0183256 | A1* | 7/2008 | Keacher ............. A61N 1/37247 607/116 |
| 2008/0221644 | A1* | 9/2008 | Vallapureddy ..... A61N 1/37247 607/60 |
| 2009/0196471 | A1* | 8/2009 | Goetz ................. A61N 1/0551 382/128 |
| 2010/0010566 | A1* | 1/2010 | Thacker ............. A61N 1/36071 607/46 |
| 2010/0121409 | A1 | 5/2010 | Kothandaraman et al. |
| 2011/0106320 | A1* | 5/2011 | Hall ...................... A01G 25/16 700/284 |
| 2012/0083857 | A1 | 4/2012 | Bradley |
| 2013/0268026 | A1 | 10/2013 | Rao et al. |

OTHER PUBLICATIONS

"U.S. Appl. No. 13/856,230, Final Office Action dated Oct. 6, 2015", 40 pgs.
"U.S. Appl. No. 13/856,230, Final Office Action dated Nov. 3, 2016", 26 pgs.
"U.S. Appl. No. 13/856,230, Non Final Office Action dated Apr. 24, 2015", 33 pgs.
"U.S. Appl. No. 13/856,230, Non Final Office Action dated May 26, 2016", 23 pgs.
"U.S. Appl. No. 13/856,230, Notice of Allowance dated Oct. 6, 2017", 15 pgs.
"U.S. Appl. No. 13/856,230, Response filed Jan. 6, 2016 to Final Office Action dated Oct. 6, 115", 12 pgs.
"U.S. Appl. No. 13/856,230, Response filed Mar. 14, 2017 to Final Office Action dated Nov. 3, 2016", 12 pgs.
"U.S. Appl. No. 13/856,230, Response filed Jul. 23, 2015 to Non Final Office Action dated Apr. 24, 2015", 11 pgs.
"U.S. Appl. No. 13/856,230, Response filed Aug. 26, 2016 to Non Final Office Action dated May 26, 2016", 12 pgs.
"Australian Application Serial No. 2013243480, First Examiner Report dated Nov. 25, 2014", 3 pgs.
"Australian Application Serial No. 2013243480, Subsequent Examiners Report dated May 7, 2015", 3 pgs.
"Australian Application Serial No. 2013243480, Subsequent Examiners Report dated Nov. 2, 2015", 3 pgs.
"European Application Serial No. 13716692.2, Office Action dated Nov. 13, 2014", 2 pgs.
"International Application Serial No. PCT/US2013/035151, International Preliminary Report on Patentability dated Oct. 16, 2014", 8 pgs.
"International Application Serial No. PCT/US2013/035151, International Search Report dated Jul. 1, 2013", 4 pgs.
"International Application Serial No. PCT/US2013/035151, Written Opinion dated Jul. 1, 2013", 6 pgs.
"Japanese Application Serial No. 2015-504710, Office Action dated Aug. 26, 2015", With Partial Translation, 3 pgs.
"Japanese Application Serial No. 2015-504710, Response filed Dec. 28, 2015 to Office Action dated Aug. 26, 2015", (English Translation of Claims), 9 pgs.
"European Application Serial No. 13716692.2, Communication Pursuant to Article 94(3) EPC dated Nov. 15, 2018", 4 pgs.
"European Application Serial No. 13716692.2, Response filed Mar. 26, 2019 to Communication Pursuant to Article 94(3) EPC dated Nov. 15, 2018", 17 pgs.

* cited by examiner

NEUROSTIMULATION SYSTEM AND METHOD FOR CONSTRUCTING STIMULATION PROGRAMS

RELATED APPLICATION DATA

The present application is a continuation of U.S. application Ser. No. 13/865,230, filed Apr. 3, 2013, which claims the benefit under 35 U.S.C. § 119 to U.S. provisional patent application Ser. No. 61/621,296, filed Apr. 6, 2012. The foregoing applications are hereby incorporated by reference into the present application in their entirety.

FIELD OF THE INVENTION

The present invention relates to tissue stimulation systems, and more particularly, to a system and method for programming an implantable tissue stimulator.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) and Peripheral Nerve Field Stimulation (PNFS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device (typically, in the form of a hand-held remote control) to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode combinations).

As briefly discussed above, an external control device can be used to instruct the neurostimulator to generate electrical stimulation pulses in accordance with the selected stimulation parameters. Typically, the stimulation parameters programmed into the neurostimulator can be adjusted by manipulating controls on the external control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

However, the number of electrodes available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby exponentially increasing the number of stimulation parameters sets available for programming.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets. The computerized programming system may be operated by a clinician attending the patient to program the neurostimulator with stimulation parameter sets in several scenarios.

For example, in order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy.

When electrical leads are implanted within the patient, the computerized programming system, in the context of an operating room (OR) mapping procedure, may be used to instruct the neurostimulator to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neurostimulator, with a set of stimulation parameters that best addresses the painful site. Thus, the navigation session may be used to pinpoint the stimulation region or areas correlating to the pain. Such programming ability is particularly advantageous for targeting the tissue during implantation, or after implantation should the leads gradually or unexpectedly move that would otherwise relocate the stimulation energy away from the target site, or if the pain pattern has worsened or otherwise changed. By reprogramming the neurostimulator (typically by independently varying the stimulation energy on the electrodes), the stimulation region can often be moved back to the effective pain site without having to re-operate on the patient in order to reposition the lead and its electrode array. When adjusting the stimulation region relative to the tissue, it is desirable to make small changes in the proportions of current, so that changes in the spatial recruitment of nerve fibers will be perceived by the patient as being smooth and continuous and to have incremental targeting capability.

During a programming session for a neurostimulator, it is very common to have several stimulation parameters sets that a patient prefers for therapy. For example, in the case of SCS, several stimulation parameter sets may be effective to treat lower back pain for a patient. As another example, the patient may suffer chronic pain in the lower back, the left thigh, and right leg, in which case, several parameter sets may be required to effectively treat the pain in these different areas. In either case, the multiple stimulation parameter sets may be combined into a single stimulation program, the activation of which will cycle through the different stimulation parameter sets in order to treat the disorder or disorders. These stimulation programs can be stored in the remote control for use by the patient in commanding the implanted neurostimulator to provide therapy in accordance with any one of the stimulation programs.

One known computerized programming system for SCS is called the Bionic Navigator®, available from Boston Scientific Neuromodulation Corporation. The Bionic Navigator® is a software package that operates on a suitable PC and allows clinicians to program stimulation parameters into an external handheld programmer (referred to as a remote control). Each set of stimulation parameters, including fractionalized current distribution to the electrodes (as percentage cathodic current, percentage anodic current, or off), may be stored in both the Bionic Navigator® and the remote control and combined into a stimulation program that can then be used to stimulate a single or multiple regions within the patient.

Prior to creating the stimulation programs, the Bionic Navigator® may be operated by a clinician in a "manual programming mode" to manually select the percentage cathodic current and percentage anodic current flowing through the electrodes, or may be operated by the clinician in an "automated programming mode" to electrically "steer" the current along the implanted leads in real-time (e.g., using a joystick or joystick-like controls), thereby allowing the clinician to determine the most efficacious stimulation parameter sets that can then be stored and eventually combined into stimulation programs. Oftentimes, the Bionic Navigator® is operated in both the manual programming mode and the automated programming mode to find an optimum stimulation parameter set.

In conventional programming systems, stimulation parameter sets are typically constructed and collected in association with only one stimulation program at a time. It is often desired to incorporate a particular stimulation parameter set into several stimulation programs or at least have the flexibility of moving a stimulation parameter set between different stimulation programs. However, because the stimulation parameter sets are constructed and combined on a program-by-program basis, it is difficult to incorporate a particular stimulation parameter set into multiple stimulation programs or move the stimulation parameter set between stimulation programs.

In some neurostimulation systems, in order to address the desire for patients to use different stimulation programs based on the time of day and/or day of the week, neurostimulators may be programmed to delivery therapy in accordance with a fixed schedule. For example, a first stimulation program may be automatically operated to provide neurostimulation therapy during a certain period in the daytime, while a second program may be automatically operated to provide neurostimulation therapy during a certain period in the nighttime. In order to program neurostimulators in accordance with a fixed schedule, several steps, including textual input, must be performed to associate each stimulation program with a particular time period and day of the week.

There, thus, remains a need to provide an improved means for incorporating stimulation parameter sets into stimulation programs and scheduling delivery of therapy in accordance with these stimulation programs.

SUMMARY OF THE INVENTION

In accordance with a first aspect of the present invention, an external control device for use with a stimulation system is provided. The external control device comprises a user interface configured for receiving input from a user (e.g., via a mouse, trackball, touchpad, and joystick, or a digitizer screen). The user interface includes a display screen configured for displaying graphical parameter objects respectively corresponding to stimulation parameter sets, and displaying graphical program objects respectively corresponding to stimulation programs. Each of the stimulation parameter sets may include, e.g., an electrode combination and/or a pulse amplitude, a pulse width, and a pulse rate. The display screen may optionally be configured for displaying stimulation parameter values within each of the graphical parameter objects.

The external control device further comprises at least one controller/processor configured for, in response to a first input from the user, selecting a first one of graphical parameter objects, dragging the first selected graphical parameter object, dropping the first dragged graphical parameter object into a first one of the graphical program objects, and storing the stimulation parameter set corresponding to the first dropped graphical parameter object in association with the stimulation program corresponding to the first graphical program object. The controller/processor(s) may be configured for selecting the first graphical parameter object by coupling a pointing device to the first selected graphical parameter object, dragging the first selected graphical parameter object by moving the pointing device across the display screen, and dropping the first dragged graphical parameter object into the first graphical program object by decoupling the pointing device from the first dragged graphical parameter object.

The controller/processor(s) may be further configured for automatically instructing the neurostimulation device to convey a stimulus (e.g., electrical energy) in accordance with a stimulation parameter set corresponding to the first dropped graphical parameter object. The controller/processor(s) may be further configured for, in response to a second input from the user, selecting a second one of graphical parameter objects, dragging the second selected graphical parameter object, dropping the second dragged graphical parameter object into the first graphical program object, and storing the stimulation parameter set corresponding to the second dropped graphical parameter object along with the stimulation parameter set corresponding to the first dropped graphical parameter object in association with the stimulation program corresponding to the first graphical program object.

In an optional embodiment, the user interface is configured for displaying a graphical parameter creation object, in which case, the controller/processor may be further configured for, in response to a second input from the user, actuating the graphical parameter creation object, displaying a stimulation parameter set creation panel on the user interface that allows a user to create an additional stimulation parameter set, and generating an additional graphical parameter object corresponding to the additional stimulation parameter set. In another optional embodiment, the controller/processor(s) is further configured for, in response to a second input from the user, actuating one of the graphical parameter objects, and displaying a stimulation parameter modification panel on the user interface that allows a user to modify the stimulation parameter set corresponding to the actuated graphical parameter object.

In another optional embodiment, the controller/processor(s) is further configured for displaying a program summary panel that displays a summary of each stimulation parameter set stored in association with the stimulation program corresponding to the first graphical program object. The program summary panel may include first and second icons for each stimulation parameter set stored in association with the stimulation program corresponding to the first graphical program object, in which case, the controller/processor(s) may be further configured for, in response to a second input from the user, actuating the first icon to deactivate the respective stimulation parameter set, and actuating the second icon to activate the respective stimulation parameter set.

In accordance with a second aspect of the present inventions, another external control device for use with a stimulation system is provided. The external control device comprises a user interface configured for receiving input from a user (e.g., via a mouse, trackball, touchpad, and joystick, or a digitizer screen). The user interface includes a display screen configured for displaying graphical program objects respectively corresponding to stimulation programs, and displaying a first graphical schedule object. Each of the stimulation programs may comprise a plurality of stimulation parameter sets.

The external control device further includes controller/processor(s) configured for, in response to a first input from the user, selecting a first one of the graphical program objects, dragging the first selected graphical program object, dropping the first dragged graphical program object into a first time period of the first graphical schedule object, and storing the first time period in association with the stimulation program corresponding to the first graphical program object. The controller/processor(s) may be configured for selecting the first graphical program object by coupling a pointing device to the first selected graphical program object, dragging the first selected graphical program object by moving the pointing device across the display screen, and dropping the first dragged graphical program object into the first graphical schedule object by decoupling the pointing device from the first dragged graphical program object.

In one embodiment, the controller/processor(s) is further configured for, in response to a second input from the user, dragging the first dropped graphical program object in the graphical schedule object to modify the first time period (e.g., by dragging only one edge of the first dropped graphical program object to change only the beginning or the end of the first time period and/or dragging the center of the first dropped graphical program object to shift the first time period), and storing the first modified time period in association with the stimulation program corresponding to the first graphical program object.

The user interface may be further configured for displaying a second graphical schedule object, and the controller/processor(s) may be further configured for, in response to a second input from the user, selecting the first graphical program object, dragging the first selected graphical program object, dropping the first dragged graphical program object into a second time period of the second graphical schedule object, and storing the first time period, along with the second time period, in association with the stimulation program corresponding to the first graphical program object. The controller/processor(s) may be further configured for, in response to a second input from the user, selecting a second one of graphical program objects, dragging the second selected graphical program object, dropping the second dragged graphical program object into a second time period of the first graphical schedule object, and storing the second time period in association with the stimulation program corresponding to the second graphical program object.

In an optional embodiment, the user interface is further configured for displaying a graphical calendar (e.g., a weekly calendar having seven days), in which case, the controller/processor(s) is further configured for, in response to a second input from the user, dragging the first graphical schedule object, dropping the first dragged graphical schedule object into a day of the graphical calendar, and storing the day in association with the stimulation program corresponding to the first graphical program object.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
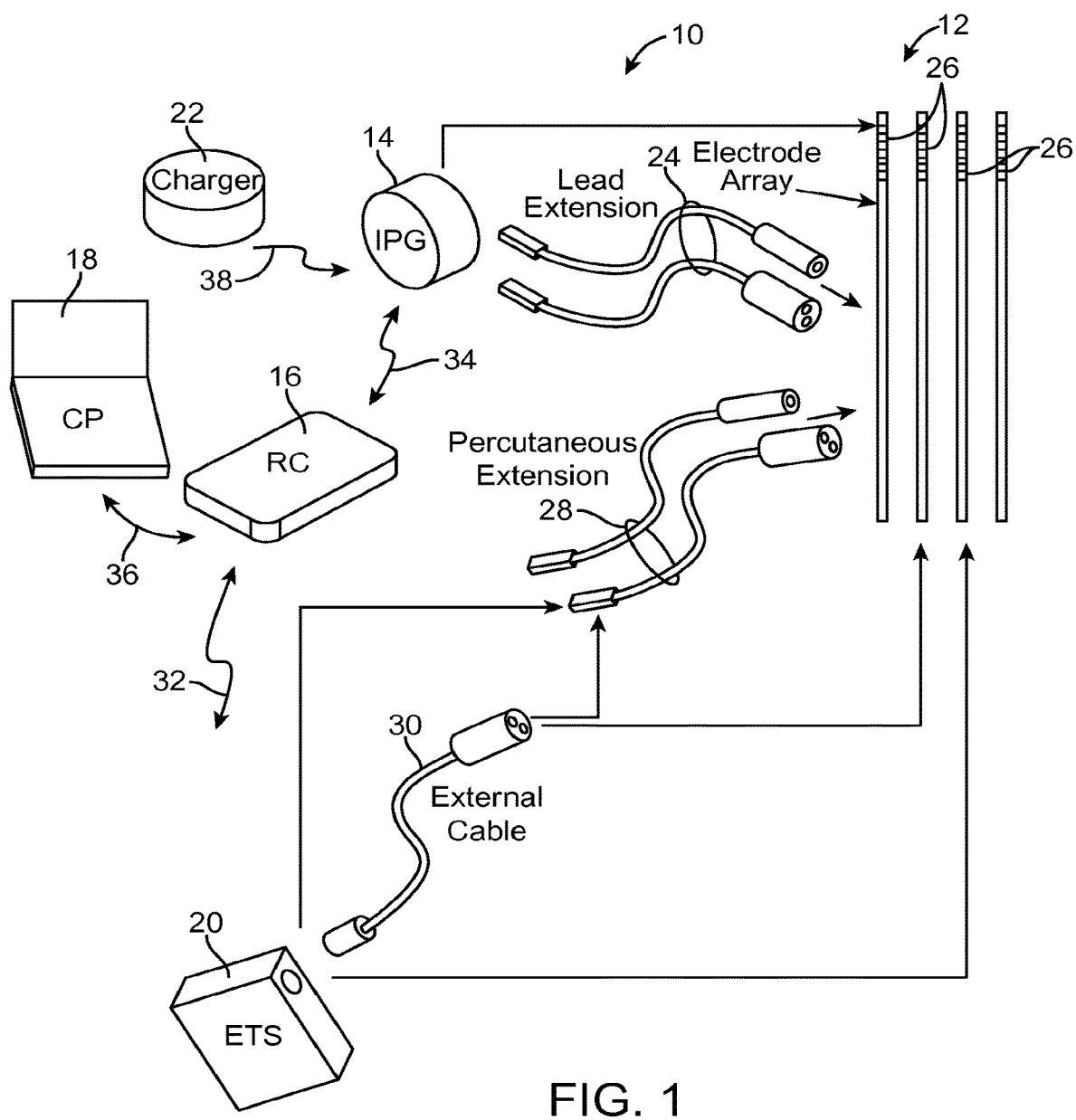
FIG. 1 is perspective view of one embodiment of an SCS system arranged in accordance with the present inventions.

Turning first to FIG. 1, an exemplary SCS system 10 generally includes a plurality (in this case, four) of implantable neurostimulation leads 12, an implantable pulse generator (IPG) 14, an external remote controller RC 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. Alternatively, a surgical paddle lead can be used in place of or in addition to the percutaneous leads. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Once the IPG 14 has been programmed, and its power source has been charged by the external charger 22 or otherwise replenished, the IPG 14 may function as programmed without the RC 16 or CP 18 being present.

For purposes of brevity, the details of the IPG 14, ETS 20, and external charger 22 will not be described herein. Details of exemplary embodiments of these devices are disclosed in U.S. Pat. No. 6,895,280, which is expressly incorporated herein by reference.

Figure 2:
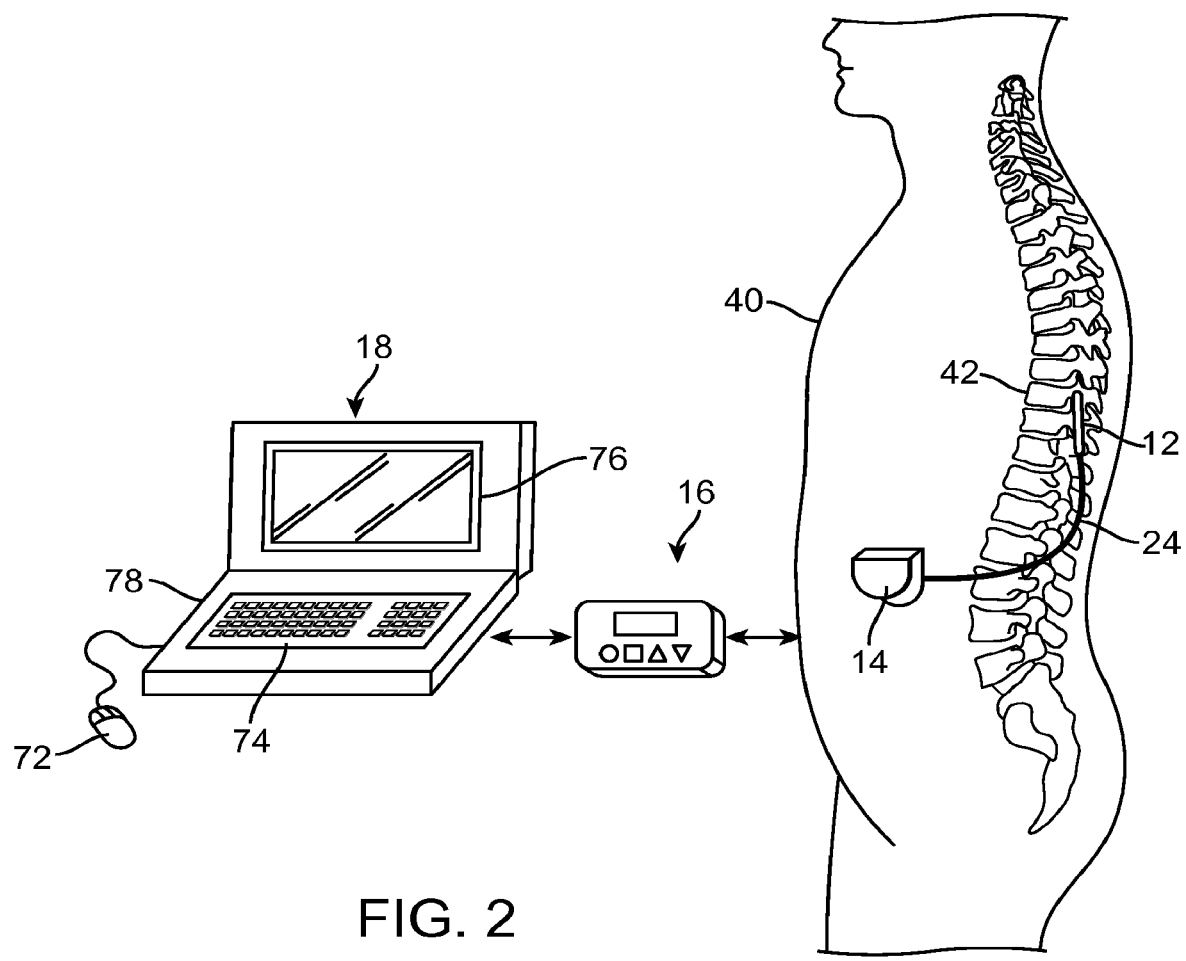
FIG. 2 is a plan view of the SCS system of FIG. 1 in use with a patient.

As shown in FIG. 2, the neurostimulation leads 12 are implanted within the spinal column 42 of a patient 40. The preferred placement of the neurostimulation leads 12 is adjacent, i.e., resting upon, the spinal cord area to be stimulated. Due to the lack of space near the location where the neurostimulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neurostimulation leads 12. As there shown, the CP 18 communicates with the IPG 14 via the RC 16.

Figure 3:
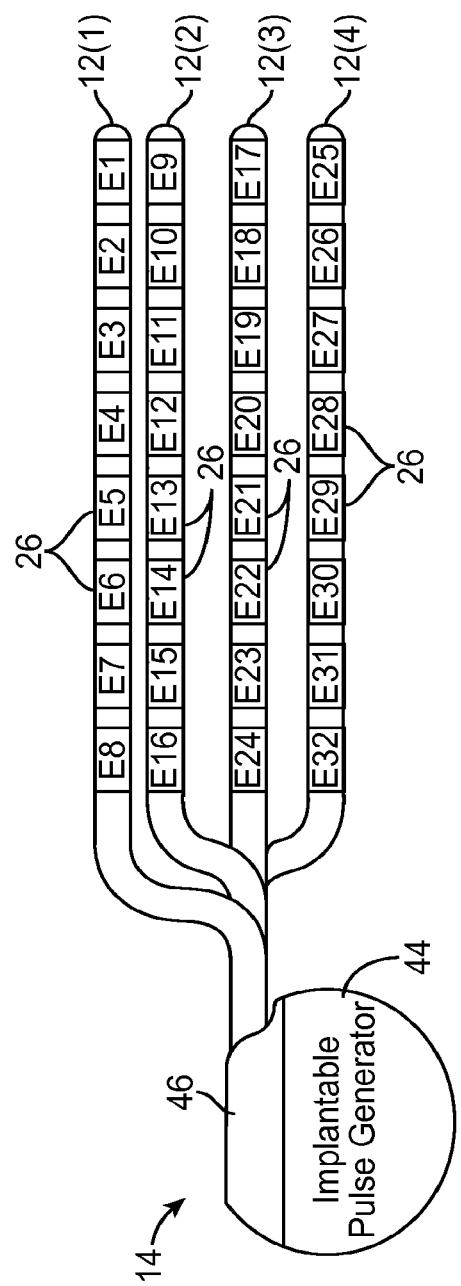
FIG. 3 is a side view of an implantable pulse generator and a pair of stimulation leads that can be used in the SCS system of FIG. 1.

Referring now to FIG. 3, the external features of the neurostimulation leads 12 and the IPG 14 will be briefly described. A first neurostimulation lead 12(1) has eight electrodes 26 (labeled E1-E8), a second neurostimulation lead 12(2) has eight electrodes 26 (labeled E9-E16), a third neurostimulation lead 12(3) has eight electrodes 26 (labeled E17-E24), and a fourth neurostimulation lead 12(4) has eight electrodes 26 (labeled E24-E32). The actual number and shape of leads and electrodes will, of course, vary according to the intended application. The IPG 14 comprises an outer case 44 for housing the electronic and other components (described in further detail below), and a connector 46 to which the proximal ends of the neurostimulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
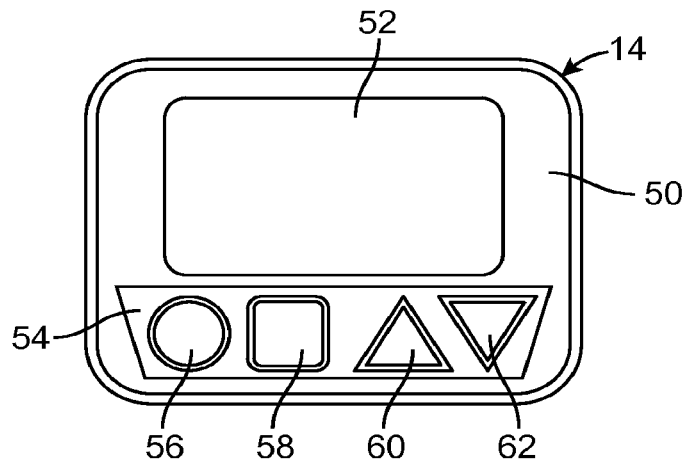
FIG. 4 is a plan view of a remote control that can be used in the SCS system of FIG. 1.

Referring now to FIG. 4, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 5:
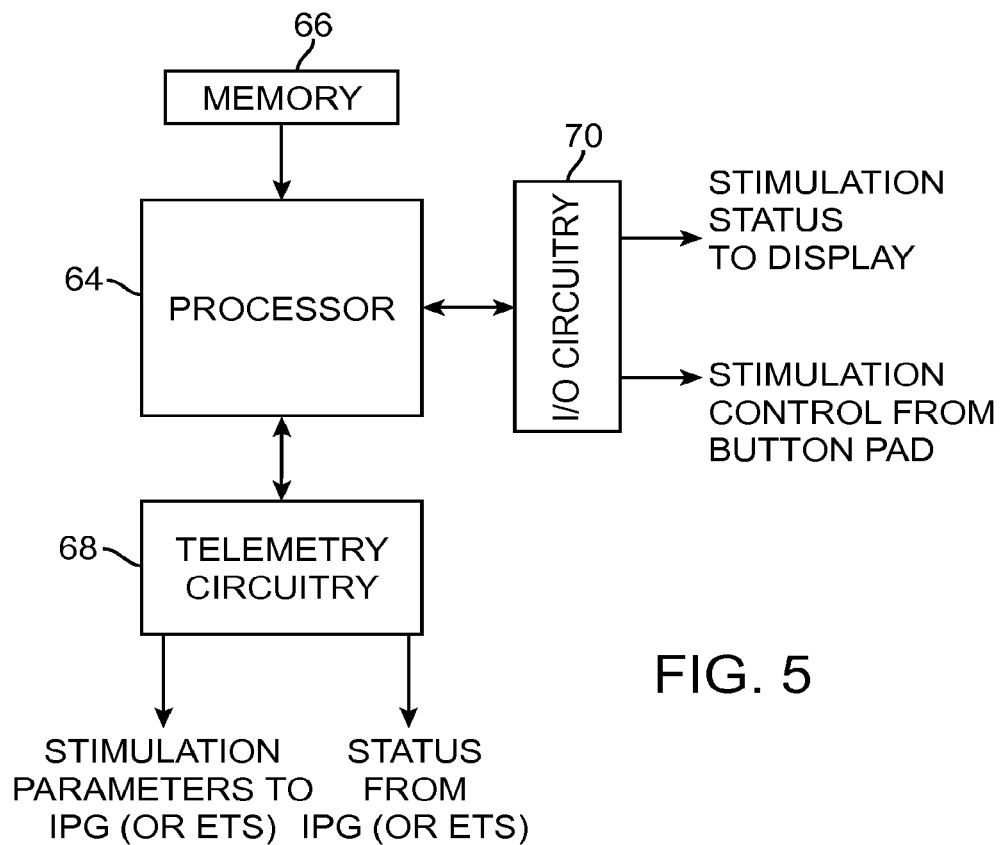
FIG. 5 is a block diagram of the internal componentry of the remote control of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets in a navigation table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implanted using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

Figure 6:
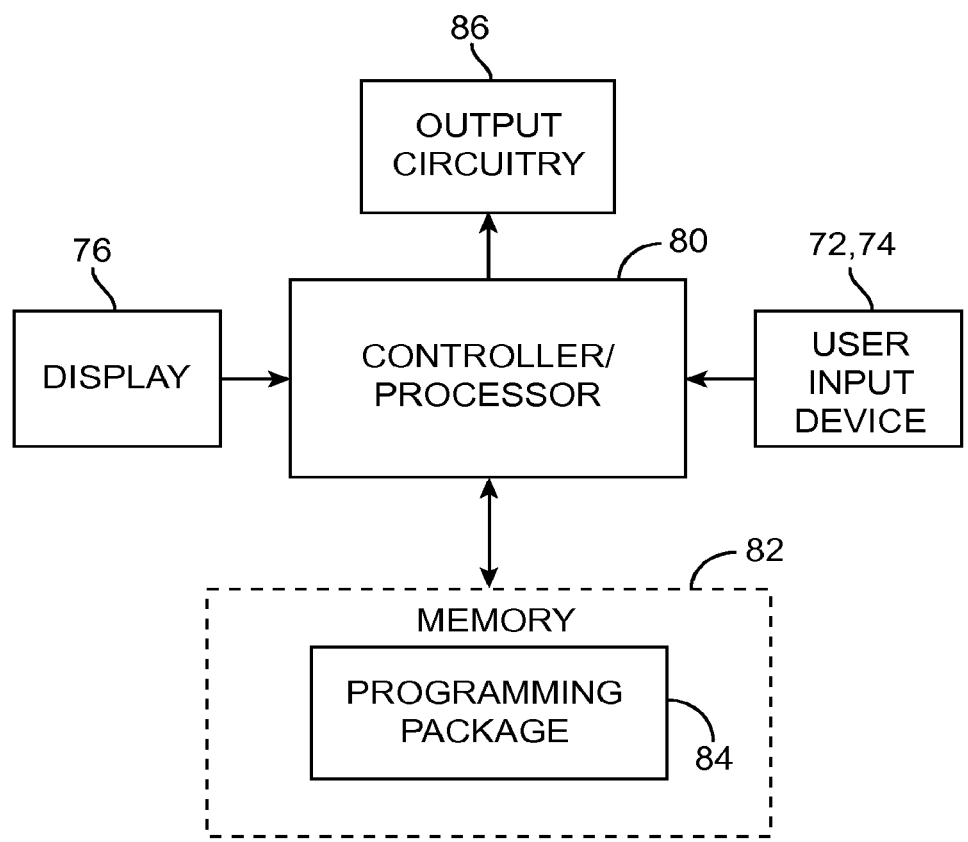
FIG. 6 is a block diagram of the components of a clinician programmer that can be used in the SCS system of FIG. 1.

To allow the user to perform these functions, the CP 18 includes a mouse 72, a keyboard 74, and a display screen 76 housed in a case 78. In the illustrated embodiment, the display screen 76 is a conventional screen. It is to be understood that in addition to, or in lieu of, the mouse 72, other directional programming devices may be used, such as a trackball, touchpad, or joystick, can be used. Alternatively, instead of being conventional, the display screen 76 may be a digitizer screen, such as touchscreen) (not shown), may be used in conjunction with an active or passive digitizer stylus/finger touch. As shown in FIG. 6, the CP 18 generally includes a controller/processor 80 (e.g., a central processor unit (CPU)) and memory 82 that stores a stimulation programming package 84, which can be executed by the controller/processor 80 to allow the user to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16. Notably, while the controller/controller/processor 80 is shown in FIG. 6 as a single device, the processing functions and controlling functions can be performed by a separate controller and processor. Thus, it can be appreciated that the controlling functions described below as being performed by the CP 18 can be performed by a controller, and the processing functions described below as being performed by the CP 18 can be performed by a processor.

Execution of the programming package 84 by the controller/processor 80 provides a multitude of display screens (not shown) that can be navigated through. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

More pertinent to the present inventions, the user interface of the CP 18 provides a user the ability to efficiently move stimulation parameter sets into stimulation programs using a drag-and-drop technique. Each of the stimulation programs can be visualized as a "bucket" of stimulation parameter sets. In particular, the user interface of the CP 18 is configured for displaying a stimulation program configuration screen, which includes a list of graphical parameter objects respectively corresponding to stimulation parameter sets (also referred to as "areas"), and a group of graphical program objects respectively corresponding to stimulation programs. Each of the stimulation parameter sets may, e.g., comprise a fractionalized electrode combination, a pulse amplitude, a pulse width, and a pulse rate, and each of the stimulation programs may comprise up to four stimulation parameter sets.

The user interface is also configured for receiving user inputs. In response to these user inputs, and in particular, drag-and-drop manipulations, the controller/processor 80 selects, drags, and drops any of the graphical parameter objects into a selected one of the graphical program objects. In the illustrated embodiment, multiple ones of the graphical parameter objects can be selected, dragged, and dropped into the same graphical program object and/or the same graphical parameter object can be selected, dragged, and dropped into multiple graphical program objects.

The user interface may receive additional user inputs for deleting any of the graphical parameter objects and corresponding stimulation parameter sets, and prompting the user interface to display a stimulation parameter set generation screen, in which the user can generate a new stimulation parameter set and add the corresponding graphical parameter object to the list of graphical parameter objects displayed in the stimulation program configuration screen.

In response to the selection, dragging, and dropping of any graphical parameter object into any of the graphical program objects, the controller/processor 80 stores, in the memory 82, the corresponding stimulation parameter set in association with the corresponding stimulation program for subsequent use by the IPG 14 and RC 16 in providing therapy to the patient. Optionally, upon dropping a graphical parameter object into a graphical program object, the stimulation parameter set corresponding to the graphical parameter object will be automatically transmitted to the IPG 14, which will respond by sequentially delivering electrical stimulation energy in accordance with that stimulation parameter set and any other stimulation parameter sets that have been associated with that stimulation program.

Figure 7:
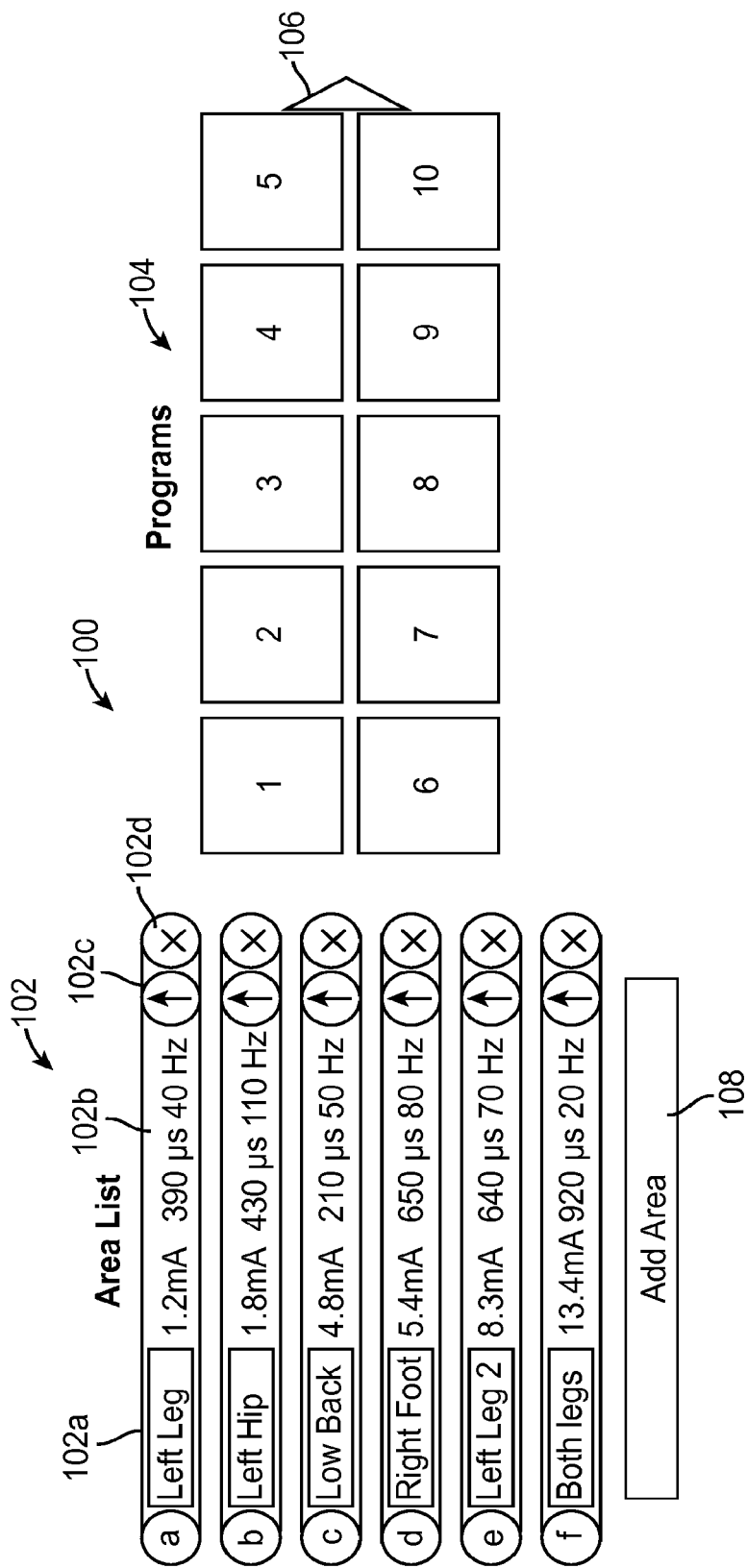
FIG. 7 is a plan view of a program configuration screen that can be displayed by the clinician programmer of FIG. 6.

As one example, and with reference to FIG. 7, a program configuration screen 100 can be used to assemble stimulation programs from any variety of stimulation parameter sets. In particular, the program configuration screen 100 includes a list of graphical parameter objects 102 corresponding to a plurality of stimulation parameter sets (or "areas") previously generated by the CP 18, and a group of graphical program objects (or "buckets") 104 corresponding to a plurality of stimulation programs, some of which may be empty (i.e., they contain no stimulation parameter sets) and some of which may be at least partially filled (i.e., they contain at least one stimulation parameter set). In the illustrated embodiment, the graphical parameter objects 102 are labeled with the letters "a," "b," etc., and the graphical program objects 104 are labeled with the numbers "1," "2," etc. In the illustrated embodiment, the shapes of the graphical parameter objects 102 and graphical program objects 104 are rectangular, although they may have different shapes.

The total number of graphical parameter objects 102 will vary, depending on how many are stimulation parameter sets are created by the user. In the illustrated embodiment, there are sixteen available stimulation programs, and thus, sixteen graphical program objects 104 (although only ten are shown). The program configuration screen 100 also includes a program scroll graphical control button 106 that can be actuated to scroll the group of graphical program objects 104 to the left. Upon scrolling the group of graphical program objects 104 to the left, the program configuration screen 100 will include another program scroll graphical control button (not shown) on the opposite side, which can be actuated to scroll the group of graphical program objects 104 to the right.

Each of the graphical parameter objects 102 contains an area descriptor 102a identifying the body region of the patient that the corresponding stimulation parameter set is intended to treat, and the electrical parameter values 102b of the corresponding stimulation parameter set, including the pulse amplitude, pulse duration, and pulse rate. For example, in the exemplary illustration, the stimulation parameter set corresponding to graphical parameter object "a" is intended to treat chronic pain in the left leg with stimulation energy having a pulse amplitude of 1.2 mA, a pulse width of 390 µs, and a pulse rate of 40 Hz; the stimulation parameter set corresponding to graphical parameter object "b" is intended to treat chronic pain in the left hip with stimulation energy having a pulse amplitude of 1.8 mA, a pulse width of 430 µs, and a pulse rate of 110 Hz; and so on. Some of the stimulation parameter sets may be intended to treat the same body region of the patient, but using different values. For example, the stimulation parameter set corresponding to graphical parameter object "e" is intended to treat chronic pain the left leg much like with the stimulation parameter set corresponding to graphical parameter object "a," but with different electrical parameter values.

Each of the graphical parameter objects 102 also contains an area modification button 102c (in the form of a circled arrow in the illustrated embodiment) that can be actuated to display an area modification screen (not shown), which can be used to either adjust the stimulation parameter set associated with the respective graphical parameter object 102 or to view stimulation parameters that are not displayed in the respective graphical parameter object 102, such as the fractionalized electrode combination. The area modification screen can be manipulated to adjust any of the stimulation parameters, including the fractionalized electrode combination, in much the same way as the stimulation parameters are adjusted in the programming screens described in U.S. patent application Ser. No. 12/501,282, which has previously been incorporated by reference. Each of the of the graphical parameter objects 102 also contains an area deletion button 102d (in the form of a circled x in the illustrated embodiment) that can be activated to delete the respective graphical parameter object 102 and corresponding stimulation parameter set from the list.

The program configuration screen 100 further includes an add area graphical control button 108 that can be actuated to display an area (or stimulation parameter set) creation screen (not shown), which can be used to create a new stimulation parameter set corresponding to a new graphical parameter object 102 that would be added to the list. The area creation screen can be manipulated to generate new stimulation parameter sets in much the same way as the stimulation parameters are adjusted in the programming screens described in U.S. patent application Ser. No. 12/501,282, which has previously been incorporated by reference.

Figure 8:
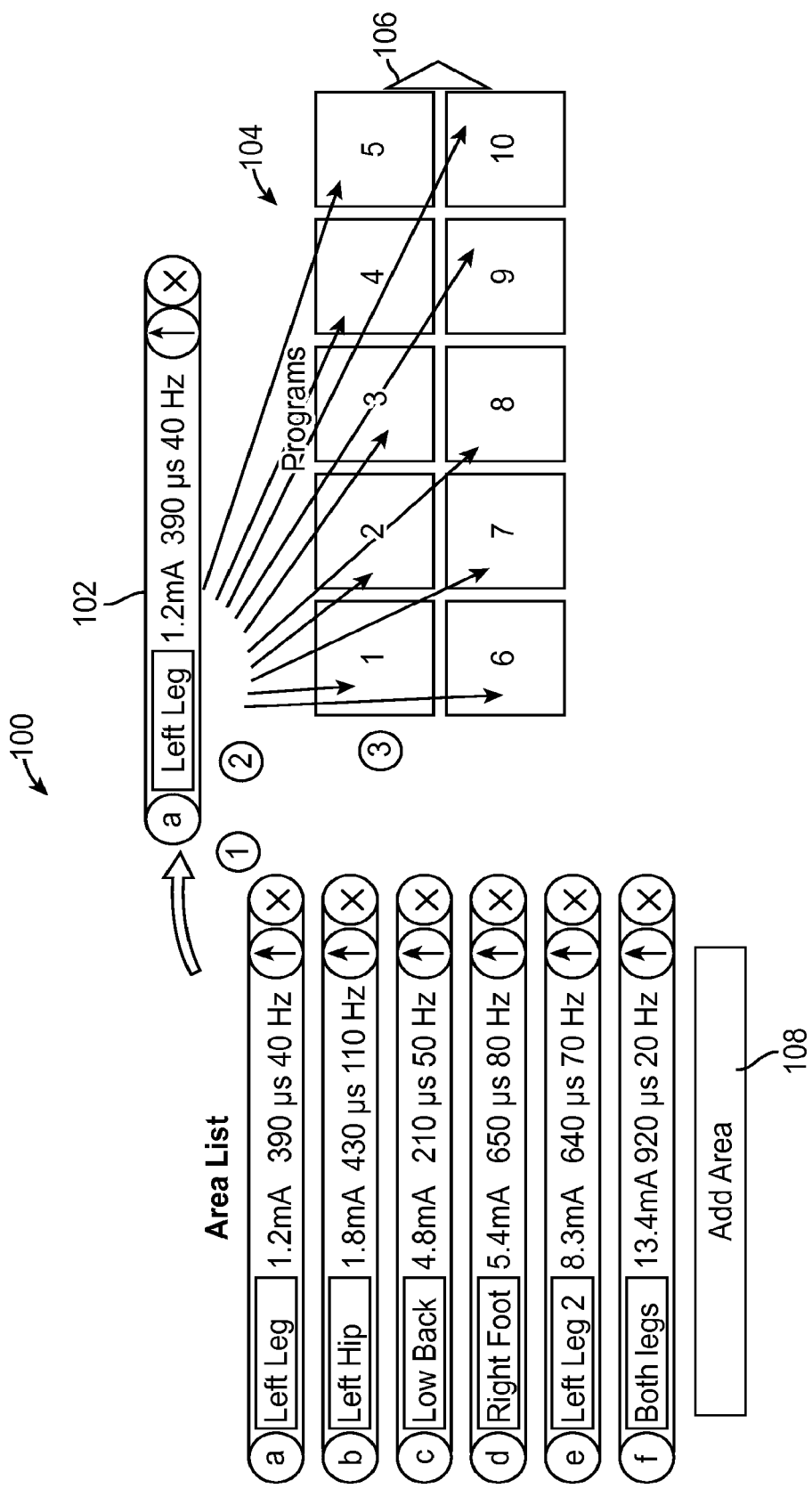
FIG. 8 is a plan view of the program configuration screen of FIG. 7, particularly illustrating a drag and drop technique used to associate a stimulation parameter set with a stimulation program.

Referring now to FIG. 8, any of the graphical parameter objects 102 can be selected, dragged, and dropped into any of the graphical program objects 104, thereby associating the stimulation parameter set corresponding to this graphical parameter object 102 with the stimulation program corresponding to the graphical program object 104 into which the graphical object was dropped. In particular, the controller/processor 80 allows a user to select one of the graphical parameter objects 102 (e.g., by coupling to one of the graphical parameter objects 102), dragging the selected graphical parameter object 102 (e.g., by displacing the selected graphical parameter object 102 towards the selected graphical program object 104), and dropping the dragged graphical parameter object 102 into the graphical program object 104 (e.g., by decoupling from the displaced graphical parameter object 102).

In the illustrated embodiment, the graphical parameter object "a" is shown via the arrows to be selected, dragged, and dropped into any of the ten available graphical program objects 102. The graphical parameter object "a" can be selected, dragged, and dropped into multiple graphical program objects 102 and/or the other graphical parameter objects "b"-"e" can be selected, dragged, and dropped into the same graphical program object 102 in which the graphical parameter object "a" is dropped. The manner in which the graphical parameter object 102 is selected, dragged, and dropped will depend on the nature of the user interface.

For example, if the display screen 76 is conventional, and a mouse 72 or other pointing device is used, the user may couple a cursor to the graphical parameter object 102 by, e.g., placing the cursor adjacent to the graphical parameter object 102 and clicking and holding on the appropriate button of the mouse 72, thereby selecting the graphical parameter object 102. The user can then move the cursor to displace the graphical parameter object 102 within the program configuration screen 100, thereby dragging the graphical parameter object 102 towards the selected graphical program object 104. Once the graphical parameter object 102 is within the graphical program object 104, the user can release the button of the mouse 72 to decouple the cursor from the graphical parameter object 102, thereby dropping the graphical parameter object 102 within the graphical program object 104.

As another example, if the display screen 76 is a digitizer screen, and a stylus or finger is used, the user may couple the stylus/finger to the graphical parameter object 102 by, e.g., placing the stylus/finger adjacent to the graphical parameter object 102 and physically touching the program configuration screen 100, thereby selecting the graphical parameter object 102. The user can then move the stylus/finger across the program configuration screen 100 to displace the graphical parameter object 102 within the screen 100, thereby dragging the graphical parameter object 102 toward the selected graphical program object 104. Once the graphical parameter object 102 is within the graphical program object 104, the user can remove the stylus/finger from the program configuration screen 100 to decouple the stylus/finger from the graphical parameter object 102, thereby dropping the graphical parameter object 102 into the graphical program object 104.

Upon dropping a graphical parameter object 102 into a graphical program object 104, the controller/processor 80 activates the stimulation program corresponding to the graphical program object 104 by instructing the IPG 14 to convey stimulation energy in accordance with the stimulation parameter set corresponding to the dropped graphical parameter object 102, in addition to any other stimulation parameter sets associated with the stimulation program. As additional graphical parameter objects 102 are dropped into the graphical program object 104, the controller/processor 80 instructs the IPG 14 to convey stimulation energy in accordance with these other stimulation parameter sets. The amplitude of the conveyed stimulation energy may be ramped up for each of the stimulation parameter sets as their corresponding graphical parameter objects 102 are dropped into the graphical program object 104. Alternatively, instead of automatically instructing the IPG 14 to convey electrical stimulation energy in accordance with the stimulation parameter sets as their corresponding graphical parameter objects 102 are dropped into a graphical program object 102, the controller/processor 80 delays this instruction until the user subsequently prompts (e.g., via actuation of an activation button (not shown)) the controller/processor 80 to deliver this instruction to the IPG 14.

Figure 9:
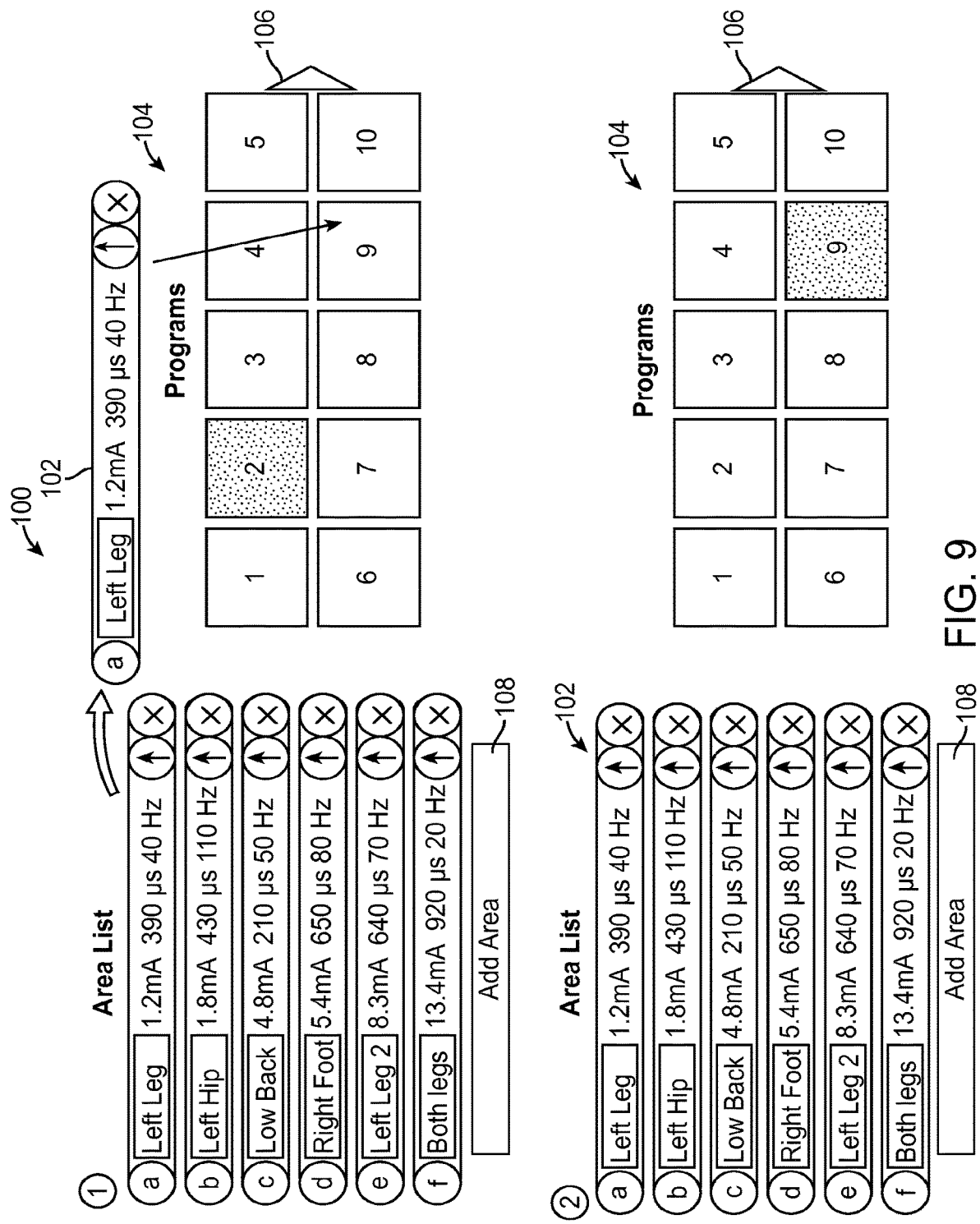
FIG. 9 is a plan view of the program configuration screen of FIG. 7, particularly illustrating a drag and drop technique to associate a stimulation parameter with multiple stimulation programs.

Upon dropping the graphical parameter object 102 into a selected one of the graphical program objects 104, the controller/processor 80 highlights the selected graphical program object 104 on the program configuration screen 100. For example, as shown in FIG. 9, graphical program object "2" is shown highlighted, indicating that corresponding stimulation program "2" is currently activated. If a graphical parameter object 102, such as graphical parameter object "a" is selected, dragged, and dropped into graphical parameter object "9", as shown in FIG. 9, the controller/processor 80 will unhighlight graphical program object "2", indicating that corresponding stimulation program "2" is currently deactivated, and will highlight graphical program object "9," indicating that corresponding stimulation program "9" is currently activated.

Figure 10:
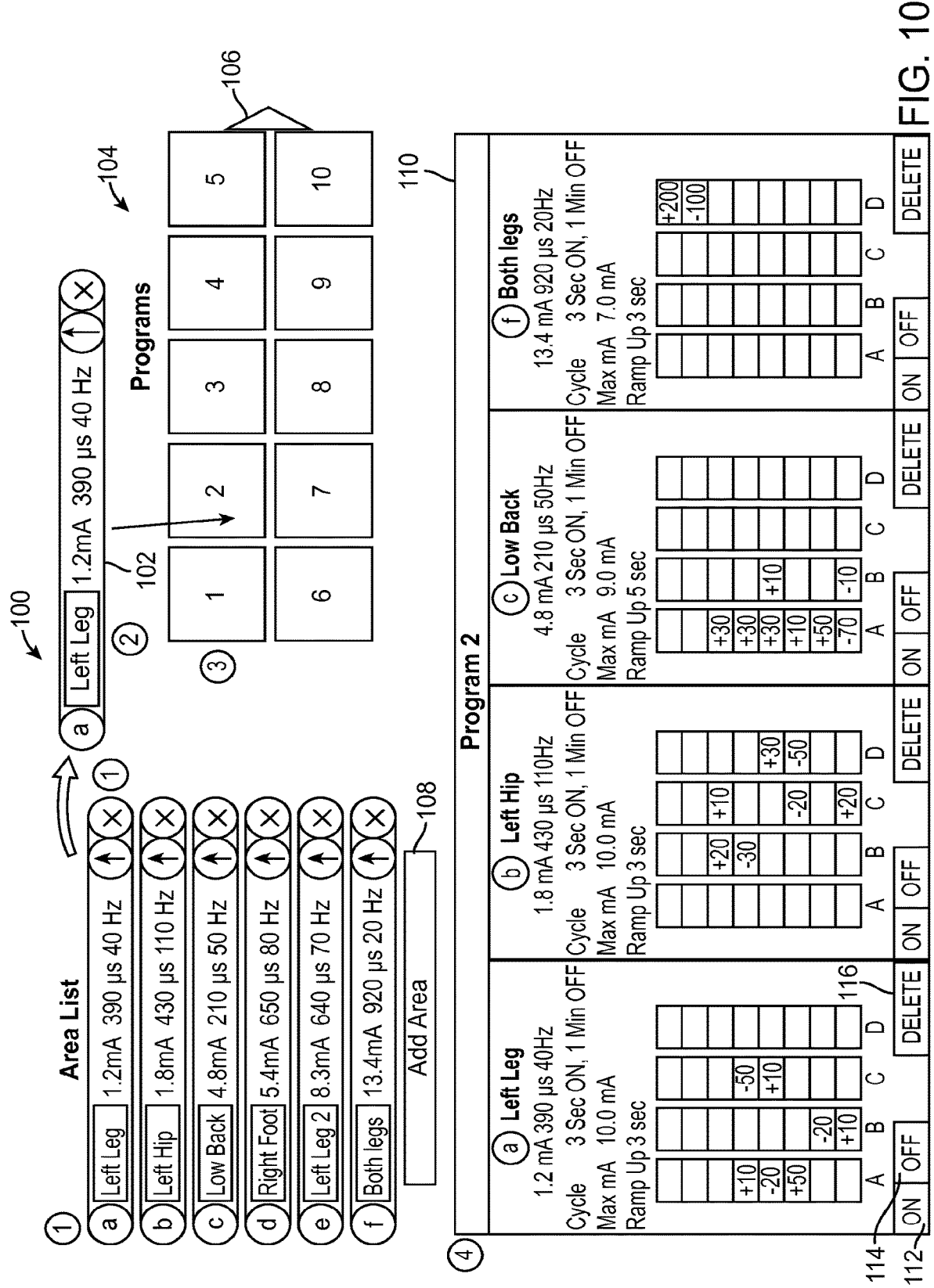
FIG. 10 is a plan view of the program configuration screen of FIG. 7, particularly illustrating a program summary panel.

Upon dropping the graphical parameter object 102 into a selected one of the graphical program objects 104, the controller/processor 80 also displays a program summary panel 110 that contains a summary of each stimulation parameter set associated with the currently activated stimulation program, as shown in FIG. 10. In the illustrated embodiment, graphical parameter object "a" is shown to be selected, dragged, and dropped into graphical program object "2," thereby prompting display of a program summary panel 110 containing a summary of the stimulation parameter sets associated with stimulation program "2." In the illustrated embodiment, the program summary panel 110 shows the pulse amplitude, pulse width, pulse rate, fractionalized electrode combination, along with other stimulation parameters including cycle time, maximum amplitude, and ramp up time. As there shown, stimulation program "2" contains four stimulation parameter sets, and in particular, stimulation parameter set "a" (left leg), stimulation parameter set "b" (left hip), stimulation parameter set "c" (lower back), and stimulation parameter set "f" (both legs).

In addition to containing a summary of the stimulation parameter sets in the respective stimulation program, the program summary panel 110 also includes, for each stimulation parameter set contained in the respective stimulation program, an "ON" icon 112 that can be actuated to activate the stimulation parameter set within the respective stimulation program (i.e., the IPG 14 conveys electrical stimulation energy in accordance with this stimulation parameter set, as well as any other activated stimulation parameter sets within the respective program), an "OFF" icon 114 that can be actuated to deactivate the stimulation parameter set within the respective stimulation program (i.e., the IPG 14 conveys electrical stimulation energy in accordance with any other activated stimulation parameter sets, but not this stimulation parameter set), and a "DELETE" icon 114 that can be actuated to disassociate the stimulation parameter set from the stimulation program.

Also pertinent to the present inventions, the user interface of the CP 18 provides a user the ability to efficiently schedule the delivery of electrical stimulation energy in accordance with multiple stimulation programs using a drag-and-drop technique.

In particular, the user interface of the CP 18 is configured for displaying a program scheduling screen, which includes a list of graphical program objects respectively corresponding to stimulation programs, and a graphical schedule object. The user interface of the CP 18 is also configured for receiving user inputs. In response to these user inputs, and in particular, drag-and-drop manipulations, the controller/processor 80 selects, drags, and drops any of the graphical program objects into a selected time period of the graphical schedule object. In the illustrated embodiment, multiple ones of the graphical program objects can be selected, dragged, and dropped into different time periods of the same graphical schedule object and/or the same graphical program object can be selected, dragged, and dropped into the same time period or different time periods of multiple graphical schedule objects.

In response to the selection, dragging, and dropping of any graphical program object into any of the graphical schedule objects, the controller/processor 80 stores, in the memory 82, the corresponding stimulation program in association with the selected time period for subsequent use by the IPG 14 and RC 16 in providing therapy to the patient. In response to additional user inputs, the controller/processor 80 drags the already dropped graphical program object in the graphical schedule to modify the time period, and stores the modified time period in association with the stimulation program corresponding to the graphical program object. For example, one edge of the dropped graphical program object can be dragged to change only the beginning or the end of the time period. As another example, the center of the dropped graphical program object is dragged to shift the time period.

Optionally, the user interface of the CP 18 is optionally configured for displaying a graphical calendar (e.g., a weekly calendar having seven days), in which case, the controller/processor 80 may be further configured for, in response to a second input from the user, dragging the graphical schedule object, dropping the dragged graphical schedule object into a day of the graphical calendar, and storing the day in association with the stimulation program corresponding to the graphical program object.

Figure 11:
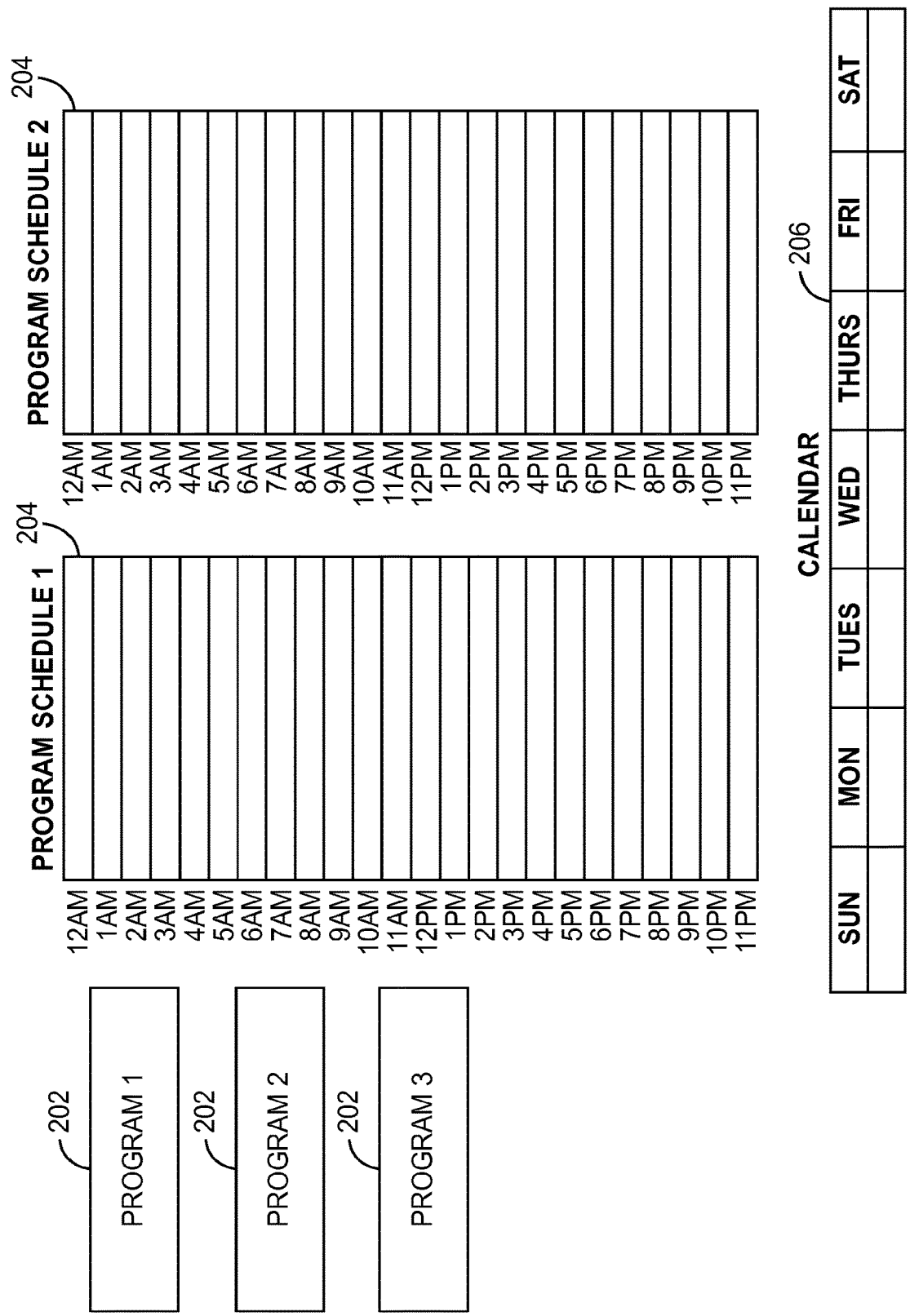
FIG. 11 is a plan view of a program scheduling screen that can be displayed by the clinician programmer of FIG. 6.

As one example, and with reference to FIG. 11, a program scheduling screen 200 can be used to schedule the delivery of electrical stimulation in accordance with several existing stimulation programs. In particular, the program scheduling screen 200 includes a list of graphical program objects 202 corresponding to a plurality of existing stimulation programs, and a plurality of graphical schedule objects 204, each including a time range. In the illustrated embodiment, the graphical program objects 202 are labeled with the letters "1," "2," etc., and the graphical schedule objects 204 are labeled with the numbers "1," "2," etc. The total number of graphical program objects 202 will vary, depending on how many stimulation programs are created by the user. In the illustrated embodiment, there are three available stimulation programs, and thus, three graphical program objects 202. Each of the graphical schedule objects 204 can be scrolled up or down to display different times of the range. The program scheduling screen 200 further includes a graphical calendar 206, which in the illustrated embodiment, is a weekly calendar having seven days (i.e., Sun-Sat).

Figure 12:
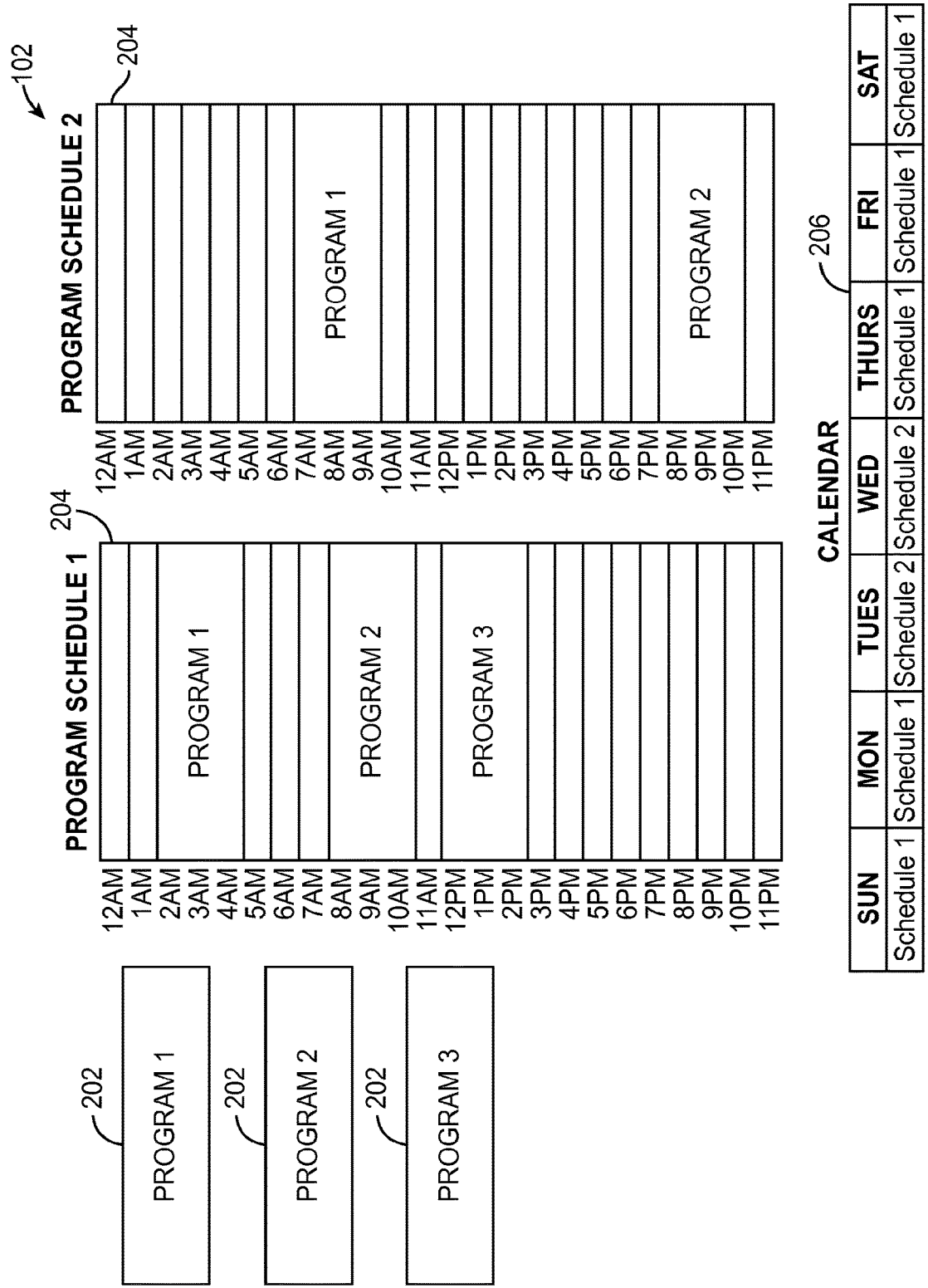
FIG. 12 is a plan view of the program configuration screen of FIG. 7, particularly illustrating a drag and drop technique to associate stimulation programs with multiple schedules.

Referring now to FIG. 12, any of the graphical program objects 202 can be selected, dragged, and dropped into a time period in any of the graphical schedule objects 204, thereby associating the stimulation program corresponding to the graphical program object 202 that was selected, dragged, and dropped with the time period. In particular, the CP 18 allows a user to select one of the graphical program objects 202 (e.g., by coupling to one of the graphical program objects 202), dragging the selected graphical program object 202 (e.g., by displacing the selected graphical parameter object 202 towards the selected graphical schedule object 204), and dropping the dragged graphical program object 202 into a time period of the graphical schedule object 204 (e.g., by decoupling from the displaced graphical program object 202). The manner in which any of the graphical program objects 202 is selected, dragged, and dropped will depend on the nature of the user interface, as discussed above with respect to the graphical parameter objects 102.

In the illustrated embodiment, three program objects 202 are shown to be selected, dropped, and dragged into graphical schedule object "1", and two program objects 202 are shown to be selected, dropped, and dragged into graphical schedule object "2." The program objects 202 are automatically defined by a two-hour time period as they are dropped into a graphical schedule object 204. Graphical program object "1" is shown in the time period 2 AM-4 AM of graphical schedule object "1" and the time period 7 AM-9 AM of graphical schedule object "2"; graphical program object "2" is shown in the time period 8 AM-10 AM of graphical schedule object "1" and the time period 8 PM-10 PM of graphical schedule object "2"; and graphical program object "3" is shown in the time period 12:00 PM-2:00 PM. Graphical schedule object "1" shown to be selected, dragged, and dropped into Sun, Mon, Thurs, Fri, and Sat of the graphical calendar 206, and graphical schedule object "2" is shown to be selected, dragged, and dropped into Tues and Wed of the graphical calendar 206.

Figure 13:
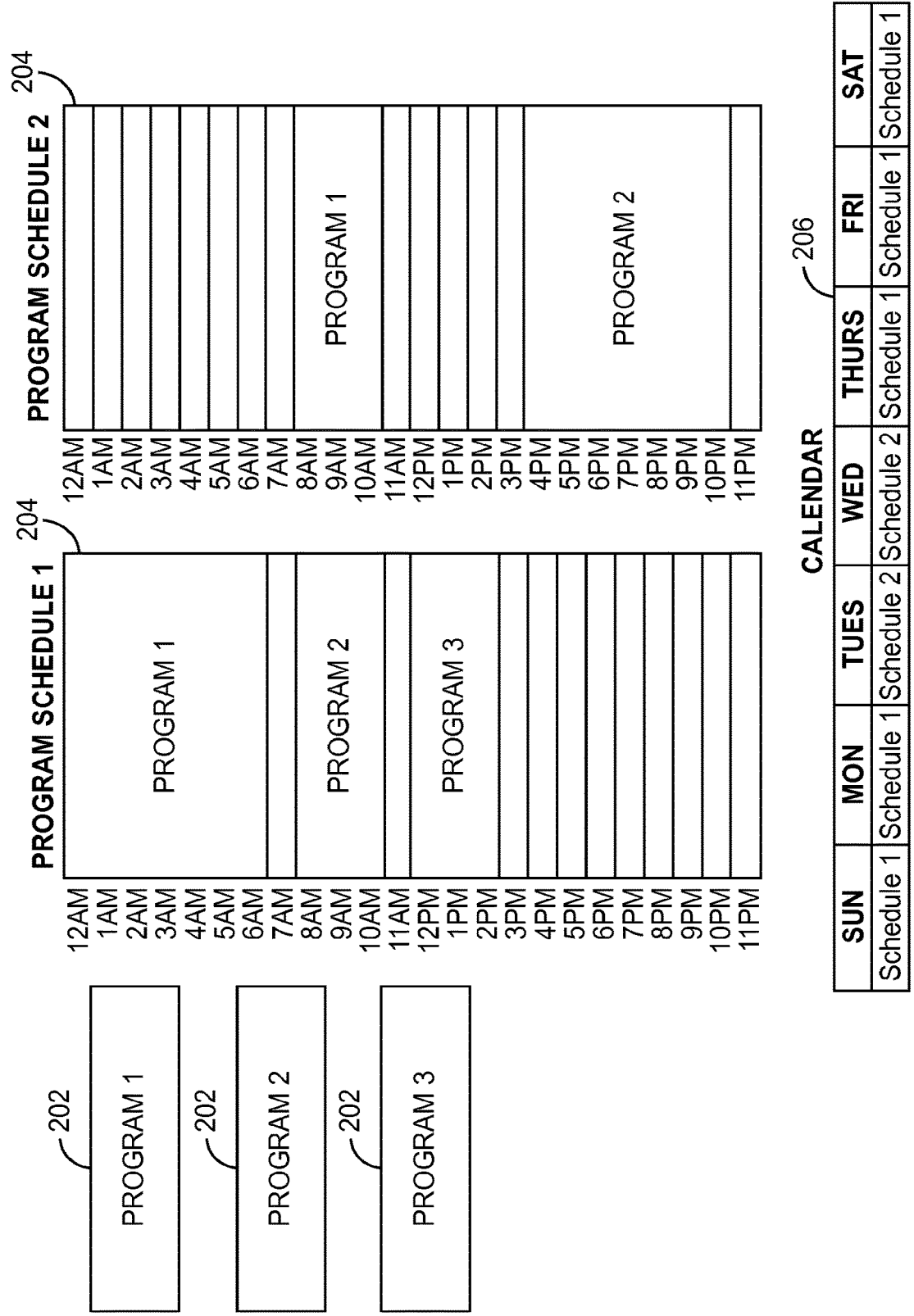
FIG. 13 is a plan view of the program configuration screen of FIG. 12, particularly illustrating a drag and drop technique to change the time periods of the stimulation programs within the multiple schedules.

As shown in FIG. 13, some of the time periods of the graphical program objects 202 by dragging the edges or centers of the graphical program objects 202. For example, in program schedule "1," the top and bottom edges of graphical program object "1" are dragged to modify the time period to 12 AM-6 AM in graphical schedule object "1." In program schedule "2," the center of program object "1" has been dragged to shift the time period 8 AM-10 AM. The top edge of graphical program object "2" has been dragged to modify the time period to 4 PM-10 PM.

Although the foregoing stimulation program configuration and scheduling techniques have been described above as being implemented in the CP 18, it should be noted that this technique may be alternatively or additionally implemented in the RC 16.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system comprising an external control device for use with a stimulation system, the external control device including:
    a user interface configured for:
    receiving input from a user, the user interface including a programming scheduling display screen with a first region and a second region;
    displaying graphical program objects respectively corresponding to stimulation programs in the first region of the programming scheduling display screen, wherein each of the existing stimulation programs includes at least one stimulation parameter set respectively corresponding to at least one targeted area of a body, each of the at least one stimulation parameter set including a corresponding fractional electrode combination configured for delivering stimulation to the corresponding targeted area of the body; and
    displaying a first graphical schedule object including a time range in the second region of the programming scheduling display screen; and
    at least one controller/processor configured for:
    selecting a first one of the graphical program objects, respectively corresponding to a first one of the existing stimulation programs including a first fractional electrode combination corresponding to a first targeted area of the body, in response to a first input from the user;
    generating a representation of dragging the first selected graphical program object;
    generating a representation of dropping the first dragged graphical program object into a first time period within the time range of the first graphical schedule object;
    storing the first time period in association with the first one of the existing stimulation programs corresponding to the first graphical program object;
    selecting a second one of the graphical program objects, respectively corresponding to a second one of the existing stimulation programs including a second fractional electrode combination corresponding to a second targeted area of the body, in response to a second input by the user;

generating a representation of dragging the second selected graphical program object;

generating a representation of dropping the second dragged graphical program object into a second time period within the time range of the first graphical schedule object;

storing the second time period in association with the second one of the existing stimulation programs corresponding to the first graphical program object;

wherein the external control device is configured to instruct the stimulation system to perform at least the first one of the existing stimulation programs corresponding to the first graphical program object to target the first area of the body during the first time period and perform the second one of the existing stimulation programs corresponding to the second graphical program object to target the second area of the body during the second time period, wherein the programming scheduling display screen includes a third region, and the user interface is further configured for displaying a graphical calendar in the third region, dragging the first graphical schedule object in response to a third input from the user, dropping the first dragged graphical schedule object into a day of the graphical calendar, and storing the day in association with the at least the first one of the existing stimulation programs corresponding to the first graphical program object, wherein the graphical calendar includes a weekly calendar.

2. The system of claim 1, wherein the at least one controller/processor is further configured for selecting the first graphical program object by representing a coupling of a pointing device to the first selected graphical program object, generating a representation of dragging the first selected graphical program object by moving the pointing device across the display screen, and generating a representation of dropping the first dragged graphical program object into the first graphical schedule object by representing a decoupling of the pointing device from the first dragged graphical program object.

3. The system of claim 1, wherein the user interface comprises one or more of a mouse, trackball, touchpad, or joystick for receiving the input from the user.

4. The system of claim 1, wherein the user interface comprises a digitizer screen for receiving the input from the user.

5. The system of claim 1, wherein the at least one controller/processor is further configured for, in response to a second input from the user, generating a representation of dragging the first dropped graphical program object in the graphical schedule object to modify the first time period, and storing the first modified time period in association with the stimulation program corresponding to the first graphical program object.

6. The system of claim 5, wherein the at least one controller/processor is further configured for generating a representation of dragging only one edge of the first dropped graphical program object to change only the beginning or the end of the first time period.

7. The system of claim 5, wherein the at least one controller/processor is further configured for dragging the center of the first dropped graphical program object to shift the first time period.

8. The system of claim 1, wherein each of the at least one stimulation parameter set includes a pulse amplitude, a pulse width, a pulse rate, and an electrode combination used by the stimulation system to deliver electrical pulses.

9. The system of claim 8, wherein the user interface is further configured to display a summary of each stimulation parameter set including an indicator of a patient body region to be treated with a stimulation parameter set.

10. The system of claim 1, wherein the graphical schedule object in the second region includes more than one daily program schedule, the programming scheduling display screen further includes a third region configured for displaying a calendar, the displayed calendar including a displayed week, the displayed week including displayed days, each of the displayed days including a displayed indicator for indicating a selected one of the more than one daily program schedule.

11. The system of claim 1, further comprising the stimulation system.

12. A non-transitory machine-readable medium including instructions, which when executed by a machine having a user interface and for use with a stimulation system, cause the machine to:

display a programming scheduling display screen on the user interface, the programming display screen including a first region and a second region;

display graphical program objects respectively corresponding to existing stimulation programs in the first region of the programming scheduling display screen, wherein each of the existing stimulation programs includes at least one stimulation parameter set respectively corresponding to at least one targeted area of a body, each of the at least one stimulation parameter set including a corresponding fractional electrode combination configured for delivering stimulation to the corresponding targeted area of the body;

display a first graphical schedule object including a time range in the second region of the programming scheduling display screen;

select a first one of the graphical program objects, respectively corresponding to a first one of the existing stimulation programs including a first fractional electrode combination corresponding to a first targeted area of the body, in response to a first input by a user, generate a representation of dragging the first selected graphical program object, generate a representation of dropping the first dragged graphical program object into a first time period within the time range of the first graphical schedule object;

store the first time period in association with the first one of the stimulation programs corresponding to the first graphical program object;

select a second one of the graphical program objects, respectively corresponding to a second one of the existing stimulation programs including a second fractional electrode combination corresponding to a second targeted area of the body, in response to a second input by the user;

generate a representation of dragging the second selected graphical program object;

generate a representation of dropping the second dragged graphical program object into a second time period within the time range of the first graphical schedule object; and store the second time period in association with the second one of the existing stimulation programs including the second fractional electrode combination to target the second area of the body corresponding to the first graphical program object;

wherein the machine is configured to instruct the stimulation system to perform at least the first one of the existing stimulation programs corresponding to the first graphical program object to target the first area of the body during the first time period and perform the second one of the existing stimulation programs corresponding to the second graphical program object to target the second area of the body during the second time period, wherein the programming scheduling display screen includes a third region, and the instructions cause the machine to display a graphical calendar in the third region, drag the first graphical schedule object in response to a third input from the user, drop the first dragged graphical schedule object into a day of the graphical calendar, and store the day in association with the at least the first one of the existing stimulation programs corresponding to the first graphical program object, wherein the graphical calendar includes a weekly calendar.

13. The non-transitory machine-readable medium of claim 12, wherein the instructions include instructions, which when executed by the machine, cause the machine to respond to another user input by generating a representation of dragging the first dropped graphical program object in the graphical schedule object to modify the first time period, and storing the first modified time period in association with the stimulation program corresponding to the first graphical program object.

14. The non-transitory machine-readable medium of claim 12, wherein the graphical schedule object in the second region includes more than one daily program schedule, the displayed graphical calendar including a displayed week, the displayed week including displayed days, each of the displayed days including a displayed indicator for indicating a selected one of the more than one daily program schedule.

15. The A method implemented by an external control device having a user interface, the method comprising:
displaying a programming scheduling display screen on the user interface, the programming display screen including a first region and a second region;
displaying graphical program objects respectively corresponding to existing stimulation programs in the first region of the programming scheduling display screen, wherein each of the existing stimulation programs includes at least one stimulation parameter set respectively corresponding to at least one targeted area of a body, each of the at least one stimulation parameter set including a corresponding fractional electrode combination configured for delivering stimulation to the corresponding targeted area of the body;
displaying a first graphical schedule object including a time range in the second region of the programming scheduling display screen;

selecting a first one of the graphical program objects, respectively corresponding to a first one of the existing stimulation programs including a first fractional electrode combination corresponding to a first targeted area of the body, in response to a first input by a user,
generating a representation of dragging the first selected graphical program object,
generating a representation of dropping the first dragged graphical program object into a first time period within the time range of the first graphical schedule object,
storing the first time period in association with the first one of the existing stimulation programs corresponding to the first graphical program object,
selecting a second one of the graphical program objects, respectively corresponding to a second one of the existing stimulation programs including a second fractional electrode combination corresponding to a second targeted area of the body, in response to a second input by the user,
generating a representation of dragging the second selected graphical program object,
generating a representation of dropping the second dragged graphical program object into a second time period within the time range of the first graphical schedule object,
storing the second time period in association with the second one of the existing stimulation programs corresponding to the first graphical program object, and
instructing a neurostimulator to perform at least the first one of the existing stimulation programs corresponding to the first graphical program object to target the first area of the body during the first time period and perform the second one of the existing stimulation programs corresponding to the second graphical program object to target the second area of the body during the second time period,
wherein the programming scheduling display screen includes a third region, the method further comprising displaying a graphical calendar in the third region, dragging the first graphical schedule object in response to a third input from the user, dropping the first dragged graphical schedule object into a day of the graphical calendar, and storing the day in association with the at least the first one of the existing stimulation programs corresponding to the first graphical program object, wherein the graphical calendar includes a weekly calendar.

16. The method of claim 15, wherein further configured for generating a representation of dragging only one edge of the first dropped graphical program object to change only the beginning or the end of the first time period, and dragging the center of the first dropped graphical program object to shift the first time period.

* * * * *